United States Patent
Arteta Montilva et al.

(10) Patent No.: US 12,100,500 B2
(45) Date of Patent: Sep. 24, 2024

(54) METHOD AND ARRANGEMENT FOR PROCESSING A SIGNAL

(71) Applicant: Optellum Limited, Oxford (GB)

(72) Inventors: Carlos Federico Arteta Montilva, Oxford (GB); Timor Kadir, Oxford (GB)

(73) Assignee: Optellum Limited, Oxford (GB)

( * ) Notice: Subject to any disclaimer, the term of this patent is extended or adjusted under 35 U.S.C. 154(b) by 624 days.

(21) Appl. No.: 17/126,934

(22) Filed: Dec. 18, 2020

(65) Prior Publication Data
US 2022/0199228 A1 Jun. 23, 2022

(51) Int. Cl.
| | |
|---|---|
| *G16H 30/20* | (2018.01) |
| *G06N 7/00* | (2023.01) |
| *G06N 20/00* | (2019.01) |
| *G06T 7/00* | (2017.01) |

(52) U.S. Cl.
CPC .............. *G16H 30/20* (2018.01); *G06N 20/00* (2019.01); *G06T 7/0012* (2013.01); *G06T 2207/20081* (2013.01); *G06T 2207/20084* (2013.01); *G06T 2207/30004* (2013.01)

(58) Field of Classification Search
CPC ...... G16H 30/20; G06N 20/00; G06T 7/0012; G06T 2207/20081; G06T 2207/20084; G06T 2207/30004
See application file for complete search history.

(56) References Cited

U.S. PATENT DOCUMENTS

| | | | |
|---|---|---|---|
| 2009/0268956 A1 | 10/2009 | Wiley | |
| 2010/0303363 A1* | 12/2010 | Fedorovskaya | G06T 7/0002 382/199 |
| 2011/0166879 A1* | 7/2011 | Lee | G16Z 99/00 705/2 |
| 2014/0072192 A1* | 3/2014 | Reiner | G16H 40/20 382/128 |
| 2020/0054306 A1 | 2/2020 | Mehanian | |
| 2020/0211678 A1* | 7/2020 | Foley | G16H 10/60 |
| 2020/0352518 A1 | 11/2020 | Lyman | |

(Continued)

OTHER PUBLICATIONS

DeVries T, Taylor GW. Learning confidence for out-of-distribution detection in neural networks. arXiv preprint arXiv:1802.04865. Feb. 13, 2018. (Year: 2018).*

(Continued)

*Primary Examiner* — Edward F Urban
*Assistant Examiner* — Duy Tran
(74) *Attorney, Agent, or Firm* — Optimus Patents US, LLC

(57) ABSTRACT

A CADx system for analysing medical images and determining if the images are acceptable for analysis, by determining if the images contain out-of-distribution input data is described. The CADx system comprises: an input circuit for receiving at least one medical image; a gatekeeper circuit for determining if the at least one received medical image contains out-of-distribution input data and so does not meet the requirements of the CADx system for acceptable images; and an output circuit to produce an output that is either a determination that the at least one received medical image contains out-of-distribution data and is not suitable for analysis by the CADx system, or a determination that the medical image is acceptable.

17 Claims, 4 Drawing Sheets

(56) References Cited

U.S. PATENT DOCUMENTS

2020/0373003 A1* 11/2020 Lyman ................ A61B 5/7275

OTHER PUBLICATIONS

Tim J Adler et al: "Out of distribution detection for intra-operative functional imaging", Arxiv.org, Cornell University Library, 201 Olin Library Cornell University Ithaca, NY 14853, Nov. 5, 2019 (Nov. 5, 2019), XP081525679, DOI: 10.1007/978-3-030-32689-0 8.
Akshay S Chaudhari et al: "Prospective Deployment of Deep Learning in MRI: A Framework for Important Considerations, Challenges, and Recommendations for Best Practices", Journal of Magnetic Resonance Imaging, Society for Magnetic Resonance Imaging, Oak Brook, IL, US, vol. 54, No. 2, Aug. 24, 2020 (Aug. 24, 2020), pp. 357-371, XP071965091, ISSN: 1053-1807, DOI: 10.1002/JMRI.27331.

* cited by examiner

METHOD AND ARRANGEMENT FOR PROCESSING A SIGNAL

FIELD OF INVENTION

This invention relates to the field of Computer Aided Diagnosis (CADx) systems and methods for assisting the interpretation of medical images to support clinicians in healthcare. In particular, the field relates to risk Computer Aided Diagnosis systems to assist the reading and reporting of medical images by radiologists and the interpretation of the radiologist's report by the physician responsible for patient care.

BACKGROUND OF INVENTION

In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, a scan provides a "dataset". The dataset comprises digital information about the value of a variable at each of a plurality of spatial locations in either a two-dimensional or (more typically) a three-dimensional space. As a specific example, a CT scan may provide images of the chest of a patient. Such a CT scan might, as a more specific example, show lung nodules in the chest.

Computer Aided Detection (CADe) devices serve to assist its users (e.g. typically clinicians) in assessing the medical images. CADe devices need to provide a clinician with standardised, objective and repeatable information. The information typically relates to particular anatomical regions, including both normal tissue and lesions, within a person. CADe devices may be used as a so-called 'Second Reader' system. Second Reader Systems are based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe device is thereby performing a second look at the scan. The results of the second look at the scan may be that the radiologist will be directed to areas of the scan that he/she had overlooked. In this way, CADe devices are designed to reduce 'false negatives', which are also termed 'missed findings'. Thus CADe devices perform a support role to clinicians.

Computer Aided Diagnosis (CADx) devices are a related technology to CADe. CADx devices attempt to solve a different problem and relate generally to risk assessment. Instead of focusing on potentially missed findings as in CADe, they try to assist the user to classify findings correctly, either as malignant or benign in the case of potentially cancerous lesions. They rely on the user to identify abnormalities, but then typically provide a score that is indicative of the risk of malignancy. There are many examples of such CADx devices proposed within the academic literature. However, few systems are available commercially, and hence used in clinical practice. This discrepancy is indicative of the difficulties in deploying practical systems with the known approaches. The output of known CADx devices is typically some kind of score. That score indicates the risk or likelihood of disease, or its absence. An example of a commercial CADx device is the 'Transpara™' product from 'Screenpoint™'. There are many non-clinical CADx devices in the academic literature.

State-of-the-art CADx devices are built around machine learning models. These models are generic algorithms with "learnable" parameters which are fitted using training data such that the model can be used to make predictions on previously unseen data. For example, a machine learning model built to predict whether a lung nodule on a CT image is malignant, can be fitted to a collection of datasets of CT images of malignant and benign lung nodules. Such a model could then be suited to assist a clinician in estimating the risk that a lung nodule they found in their practice could be malignant. The process of fitting the model parameters to the training data is referred to as the model training, while the process of using the model to make a prediction on input data is referred to as inference. The output of the inference in the case of a machine learning-based CADx device would typically be a score indicative of the likelihood that the input sample contains the disease of interest, for instance a score for malignancy in the case of the lung nodules.

A general assumption when using machine learning models is that the training data will be representative of the data used at inference time; for example, the input data the model will receive once deployed to the users, i.e. the medical personnel who will use the CADx device. When the data where the inference is done is not well-represented by the training data, i.e. it does not resemble any sample in the training data, it is said to be out-of-distribution (OOD) data. Using a machine learning model to make predictions on OOD data is considered a misuse of the model as its performance cannot be assured. That is, before being used for inference in a real setting, the model is characterised. During characterisation the frequency at which a model makes different kinds of errors when performing its task is measured and recorded in a report, for instance the frequency with which the model incorrectly classifies malignant lung nodules as benign and vice-versa may be measured. When OOD data is encountered at inference time, the model might make errors more frequently than the model characterisation will have reported, and this will not be apparent to the user, i.e. the user will make clinical decisions using a model that makes errors more often than they have been led to expect. An example of this scenario is a machine learning model for lung cancer prediction that is trained using CT images with a specific set of image acquisition and reconstruction parameters, but is used on CT data that was acquired or reconstructed differently. In such a case, the performance of the model at inference time could be worse than when the model was tested by the manufacturers.

In order to be protected against OOD data, the manufacturers of the CADx device would typically issue a set of indications for use (IFU) which aims to tell the user the type of input data that is considered valid for the system. In the context of a CADx device for estimating lung cancer diagnosis from CT images, these IFU could include specific CT acquisition protocols, scanner manufacturers and reconstruction algorithms. Such an explicit approach can help prevent users from inadvertently misusing the CADx device by inputting images that contain OOD data. However, IFU are not practical for subjective qualities of the input data such as image quality and acquisition artefacts, e.g. artefacts arising from a patient moving during a CT image acquisition. More importantly, IFU cannot cover for factors that are unknown to the CADx device manufacturer. For example, a CADx device for lung cancer diagnosis from CT images could be affected by the presence of an infection in a patient's lung that was rare at the time of model development and non-existent in the training data, but which then became highly prevalent (e.g. COVID-19). Other examples of unknown factors in the input data of a deployed CADx device could include patients with an unusual anatomy, e.g. a missing lung lobe that had been excised during an earlier surgical procedure, experimental modifications of the image acquisition protocol but which still fall within the issued IFU, or even slightly miscalibrated imaging equipment. Therefore, even in a seemingly controlled environment where a CT is acquired for the purpose of lung cancer prediction and complies with the IFU, the space of unknown factors which can make data be OOD is potentially very large, and remains an important hazard for a lung cancer CADx device.

The problem of dealing with images that contain OOD data has been a long-standing challenge in machine learning research, and will become a very relevant one for industries where machine learning is used as part of critical devices such as the autonomous vehicle industry and healthcare. In the case of CADx devices for lung cancer diagnosis, there is still a need for reliable protection against images with OOD data, for example, by preventing the machine learning model from assessing samples that it is not suited to assess.

Detecting and protecting against OOD data needs to be an automated process, for example, carried out by a purpose-built machine learning model which flags and prevents the CADx device from producing a score from OOD data. The need for automation comes from the fact that detecting OOD data requires the memorization of potentially tens of thousands of data samples that commonly make up a training data set for a state-of-the-art machine learning model. However, due to its automatic nature, the deployment of a OOD detection element within a CADx device could have unintended consequences affecting the experience of the user and their trust in the CADx device. Simply preventing the user from using the CADx device on a given sample could be unacceptable to them if they are not made aware of what characteristic of the input sample made it unfit for use. The following example illustrates such a scenario. A CADx device for lung cancer diagnosis is used to evaluate the cancer risk of a lesion found in the CT of a patient. The patient had recently undergone a lung procedure for an unrelated condition that left a visible scar close to the suspicious lung lesion. This resulted in an input sample unlike anything that was present in the training data of the machine learning model. The OOD data detection element correctly alerts the user that the input sample cannot be assessed, or that the output should not be used. Suspecting that the image quality was not optimal for the CADx device, the user attempts to run variants of the image (e.g. with different CT reconstruction parameters) leading to the same unsuccessful outcome. This experience potentially results in frustration, doubts regarding the quality of the CADx device and a reduced level of trust in its output for the cases where it does produce a cancer risk prediction.

In summary, OOD samples are a major risk when state-of-the-art CADx devices are used in clinic, even in seemingly highly controlled scenarios such as lung cancer prediction from CT images. Therefore, there is a need for detecting when OOD inputs are encountered to make the clinician aware of the risks associated with using the CADx device in this case. The OOD detection should be performed in a manner that minimizes the impact on the user experience as to maintain their trust in the CADx device, and hence the potential benefit to the patient which comes from using the CADx device.

SUMMARY OF THE INVENTION

Accordingly, the invention seeks to mitigate, alleviate or eliminate one or more of the abovementioned disadvantages singly or in any combination.

According to the invention there is provided a CADx system for analysing medical images and determining if the images are acceptable for analysis, by determining if the images contain out-of-distribution input data comprising: an input circuit for receiving at least one medical image; a gatekeeper circuit for determining if the at least one received medical image contains out of distribution input data and so does not meet the requirements of the CADx system for acceptable images; and an output circuit to produce an output that is either a determination that the at least one received medical scan image contains out-of-distribution data and is not suitable for analysis by the CADx system, or a determination that the medical scan image is acceptable.

In a preferred embodiment of the invention the output circuit further comprises: a rejection explanation generator to generate an output of why the received medical image is not suitable for analysis by the CADX system.

In a further preferred embodiment of the invention the output further comprises: a disease risk score that is output when the gatekeeper circuit determines that the at least one received medical image is acceptable for analysis by the CADx system.

In an embodiment of the invention, the input image is one of: a CT image, an MRI image, a PET image, an X-ray image, an ultrasound image or a SPECT image.

In a further embodiment of the invention the input further comprises one of more of: biomarkers for the patient or clinical parameters for the patient. Further preferably, the biomarkers and clinical parameters comprise at least one of: patient age, patient sex, results of blood tests, results of lung function tests.

In a preferred embodiment of the invention the gatekeeper circuit further comprises an input similarity estimator that can compare the received input image to a distribution model derived from training data to determine if the input image contains out-of-distribution input data. Further preferably, the distribution model is a model of the probability distribution of the training data.

In an embodiment of the invention, the input similarity estimator further comprises a second distribution model for specific out-of-distribution data, and the input similarity estimator indicates input data that is closer to the second distribution model rather than the training data.

Preferably, the input similarity estimator comprises a plurality of different distribution models, and wherein the output circuit can provide an output that the image is out-of-distribution data and also indicate which distribution model most resembles the input image with out-of-distribution data.

In a further embodiment of the invention the input circuit further comprises an input data encoder to transform the input data into a feature descriptor which comprises an intermediate numerical representation of the input data.

Preferably, the feature encoder generates the feature descriptor using a neural network.

In a further embodiment of the invention, the feature descriptor is a vector containing scalar values that encode the input data according to the strength of the patterns of data within input data that a neural network has been trained to recognise as salient to computing a disease risk score.

Preferably, the feature descriptor provides an input to a score calculator for determining a disease risk score for the input medical image. In an alternative embodiment of the invention, the feature descriptor is input to the gatekeeper circuit to determine if the input medical image is suitable for analysis by the CADx system.

In an embodiment of the invention, the feature descriptor is input to at least one of a rejection explanation generator and an input similarity estimator of the gatekeeper circuit. Preferably, at least one of the rejection explanation generator and a score calculator provide an output to an output selector.

In a further embodiment of the invention, the rejection explanation generator determines an attribution map A for the input medical image for each pixel of the image to generate the output that the image is not suitable for analysis. Preferably, the attribution map A is a matrix, with the value of each element of the matrix related to the image intensity of a pixel in the input image.

In a preferred embodiment of the invention, the rejection explanation generator determines the attribution map A by calculating the distance between the input data and the distribution model of the training data and further calculating the derivative of the distance with respect to the input image.

Preferably, the output selector will select either a disease risk score if the medical image is acceptable, or an explanation of the reason that the image is not suitable for analysis as the output from the CADx system.

In a preferred embodiment of the invention the output selector compares the output of the input similarity estimator to a threshold to determine if the input data should be rejected as containing out-of-distribution data. Preferably, the threshold is used to determine the CADx output such that:

$$\text{CADx Output} = \begin{cases} DiseaseRiskscore, & InputSimilarity \geq TH_{sim} \\ RejectionExplanation, & InputSimilarity < TH_{sim} \end{cases}$$

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

In the context of a CADx device that is based on a machine learning model to produce a disease risk score for input medical data, this invention addresses the need for gatekeeping the input data to prevent the disease prediction model from making predictions on datasets that it is not suited to assess. An embodiment of this invention is the gatekeeper, a circuit which can form part of the CADx device. The gatekeeper analyses the response of the disease prediction model to a given input data and decides whether the CADx device should reject the evaluation of the input by the disease prediction model as unfit for use. The decision to reject input data occurs when an OOD input is detected; that is, input data that differs substantially from the data used for training the disease prediction model. Therefore, when the gatekeeper rejects an input data, the user is alerted that the input data is OOD. This alert is communicated to the user instead of the score.

The CADx device with gatekeeper may optionally provide the user with further details of the reason the input data was rejected. This is achieved through a rejection explanation generation mechanism. The rejection explanation prevents the gatekeeper from negatively affecting the usability of the CADx device, which can lead to user frustration and loss of trust.

Figure 1:
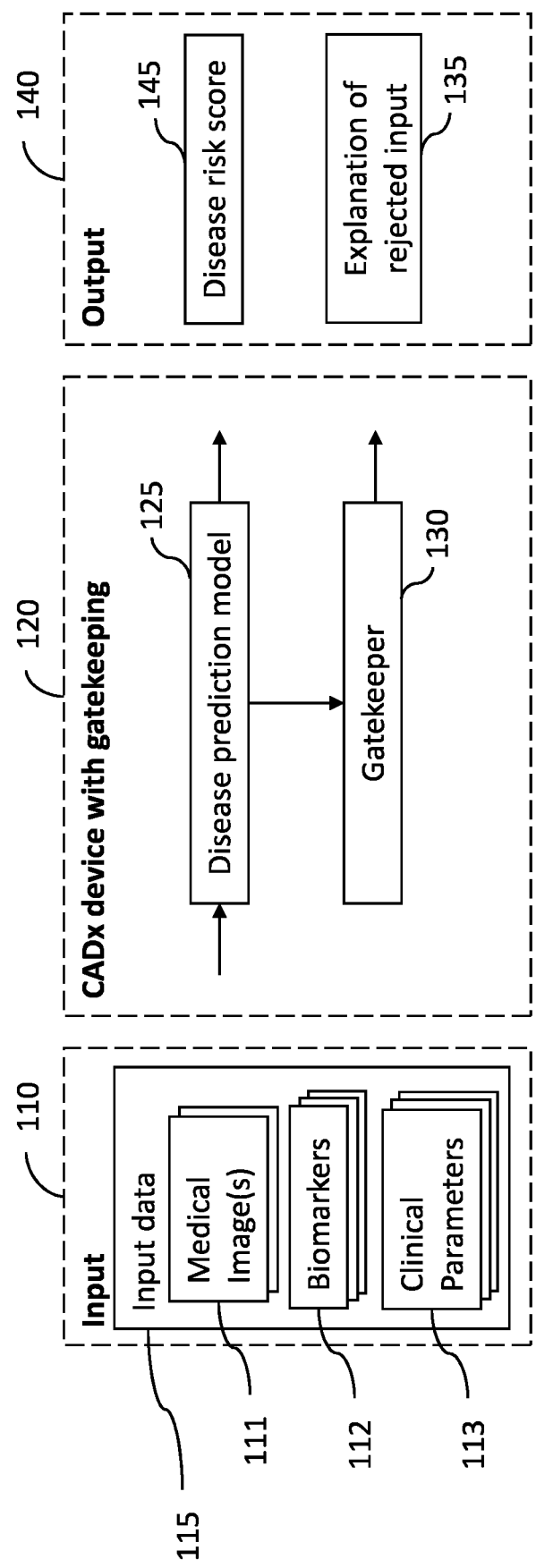
FIG. 1 illustrates a CADx system according to an embodiment of the invention.

In more detail, FIG. 1 illustrates a CADx device with gatekeeper (100): a machine learning based CADx device with a gatekeeper circuit. As shown the CADx system (100) comprises an input circuit (110), a CADx device with gatekeeper circuit (120) and output circuit (140). The input to the CADx device is a unit of input data (115) containing at least one medical image (111), preferably the medical image is one of a CT image, an MRI image, a PET image, an X-ray image, an ultrasound image or a SPECT image, possibly in combination with clinical parameters (112) such as patient age and sex, and the result of relevant tests such as biomarkers for a patient (113), e.g. a test for a gene mutation associated with an increased risk of cancer. Other examples of clinical parameters are results of blood tests, patient or family history of disease, body weight, and location of a suspicious lesion. Like standard CADx devices, when the input data (115) is presented to the input circuit (110) of the CADx device (100), the data is processed by a machine learning model (125) that is trained to predict a risk score of a disease given the input data. Specifically, the disease prediction model (125) performs a series of mathematical operations on the values of the input data resulting in a disease risk score (145) that is provided via the output circuit (140). Unlike standard CADx devices, the CADx device with gatekeeper (120) includes a gatekeeper (130), a circuit capable of determining whether the disease prediction model (125) is suited to assess the given input data (115). The gatekeeper is also based on a machine learning model trained in conjunction with the disease prediction model (125) such that it is able to determine when a unit of input data is not suitable for assessment by the disease prediction model (125). This is achieved by processing, through mathematical operations, internal values of the disease prediction model (125) resulting in a binary decision of whether the input data (115) should be rejected. When the gatekeeper (130) detects that a unit of input data should be rejected, it prevents the disease risk score from being sent to the output circuit (140). Instead, it indicates that an OOD sample was encountered. In a preferred embodiment of the invention, the output circuit may also generate and send to the output a form of explanation indicative of why the input data was rejected.

Implementation of the CADx Device with Gatekeeper

FIG. 2 shows the diagram of an example implementation of a CADx device with gatekeeper according to an embodiment of the invention. Central to the CADx device is a machine learning model for disease prediction (125) that receives medical data through the input circuit (110). In some examples of the invention, the disease prediction model first processes the input data with a feature data encoder (210), a part of the machine learning model with parameters $w_f$ which transforms the raw input data into an intermediate numerical representation called a feature descriptor (215). In some examples, the feature descriptor (215) is a vector containing scalar values $v=[v_1 \ldots v_n]$ which encode the strength with which relevant patterns, learned during the model training, appear in the input data. For instance, if the machine learning model aims to predict lung cancer from images of lung nodules, relevant features could include the size of the nodule, smoothness of the nodule boundaries, homogeneity of the image region inside the lung nodule, formation of vasculature around the nodule, and other more complex features that the machine learning model uses but cannot be articulated in human terms. Assuming the value $v_k$ in v encodes the smoothness of the nodule boundaries, then a high $v_k$ would be indicative of a smooth nodule boundary, whereas a low value of $v_k$ would indicate otherwise. In some examples, the feature descriptor (215) is transformed into a disease risk score through a score calculator, a part of the machine learning model with parameters $w_s$. The operation performed by the score calculator can take the form $$\text{DiseaseRiskScore}=f_s(v;w_s) \quad (1.1).$$

Parallel to the machine learning model for disease prediction is the gatekeeper (130). The central element of the gatekeeper is the input similarity estimator (230) whose function is to produce a measure indicative of how similar a unit of input data is to the training data of the disease prediction model (125). In some examples of the invention, the input similarity estimator (230) contains a distribution model for the training data, $P_{train}$, which defines what examples of data are common in the training data and what examples are uncommon. The input similarity estimator can then evaluate how common a new input data unit x is under $P_{train}$ as $$\text{InputSimilarity}=P_{train}(F(x);\theta) \quad (1.2).$$

In some examples of the invention, the input similarity estimator (230) is based on the parameters of a clustering model fitted to the training data (e.g., a K-means model [MacQueen, J B Proc. $5^{th}$ Berkley Symposium On Mathematics Statistics and Probability 1:281-297, 1967]). For a K-means model the input similarity value (1.2) can be defined as the distance to the centre of the nearest cluster in the model. Similarity can be defined in many ways, for instance the mean distance to the centres of the two or more nearest clusters could be used. Different kinds of distribution model can also be used in the invention, for instance Gaussian Mixture Model (GMM) [Bishop, C "Pattern recognition and machine learning". New York: Springer, 2006].

In eq. 1.2, F is a mapping function applied to the input data x and $\theta$ are the parameters of the distribution $P_{train}$.

Figure 2A:
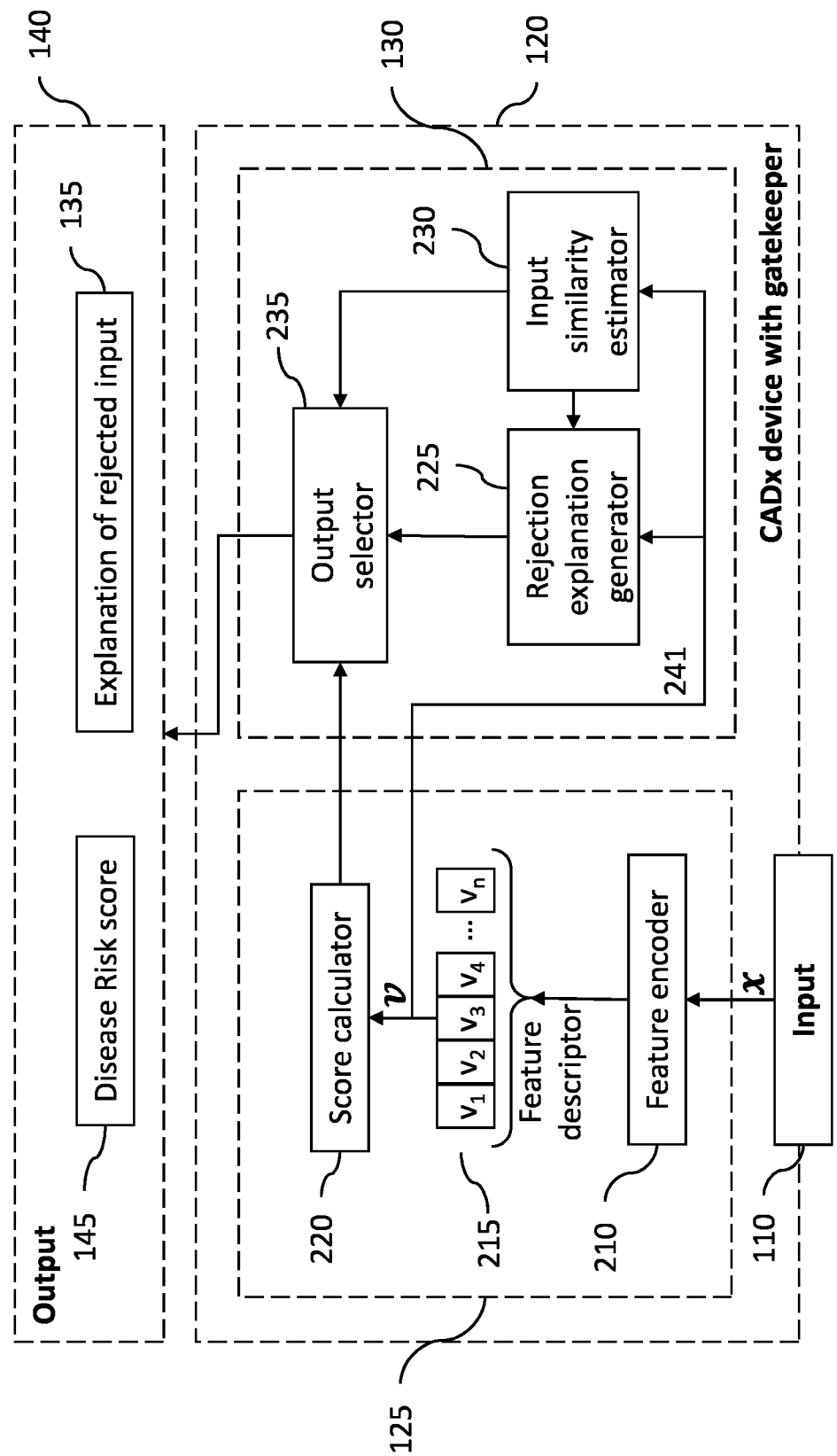
FIG. 2(a) show a high-level implementation of the CADx system with a gatekeeper circuit according to an embodiment of the invention.
Figure 2B:
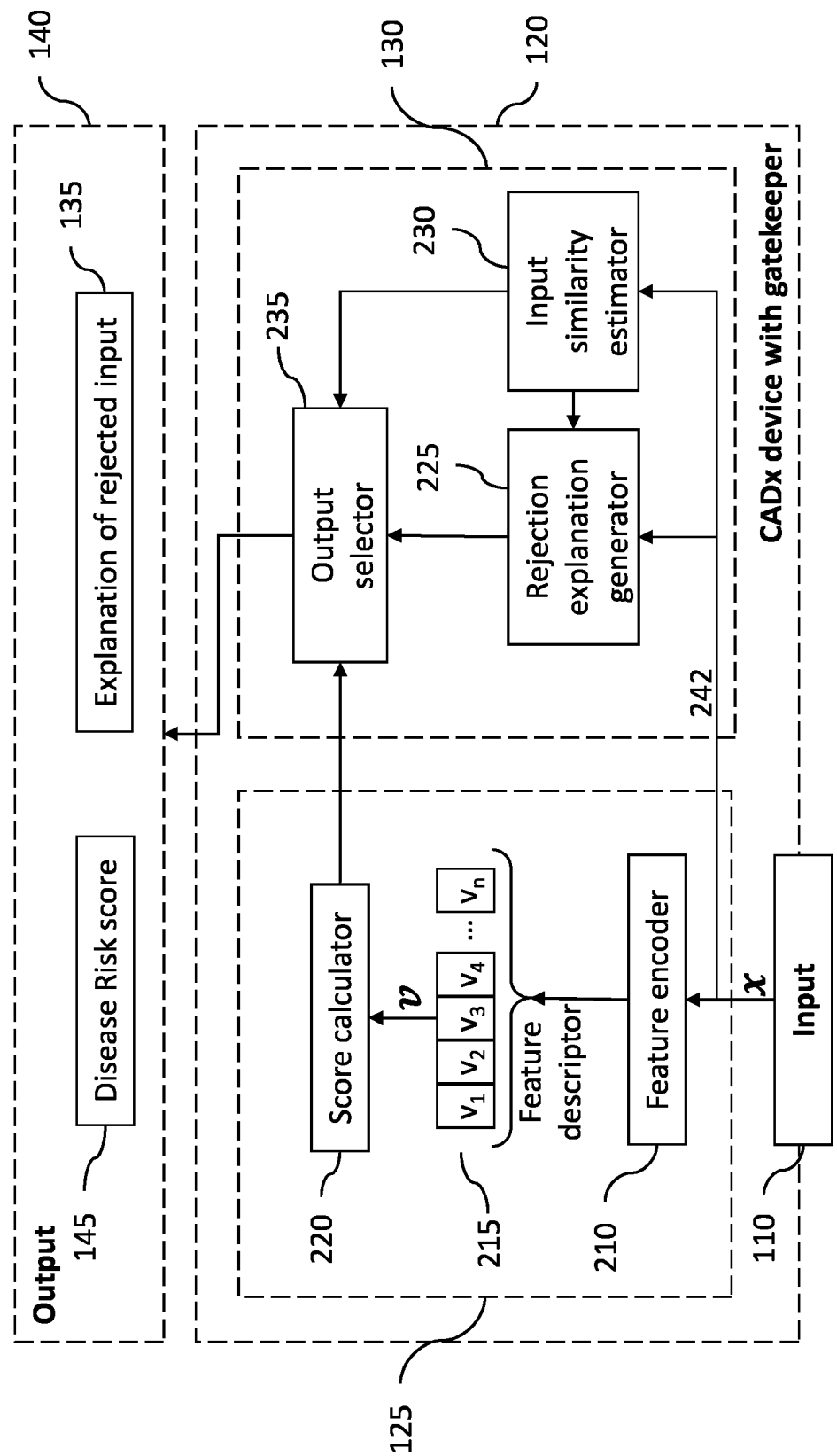
FIG. 2(b) shows an alternative high-level implementation of the CADx system with a gatekeeper circuit according to an embodiment of the invention.

In some examples of the invention (as shown in FIG. 2A), the mapping function F is the feature encoder (210) of the disease prediction model such that $F(x)=v$; that is, the input (241) to the gatekeeper (130) is the feature descriptor output by the feature encoder (215). In this case, the input similarity estimator (230) assesses the input data unit from its feature descriptor v, thus measuring the similarity of the input data's feature descriptor to the feature descriptors of the training data. In other examples of the invention (FIG. 2B), $F(x)=x$; that is, the input to the gatekeeper (130) is the input data to the feature encoder (242), thus the input similarity measure (230) assesses the input data in its raw form, A CADx device equipped with a gatekeeper (130) comprising of an input similarity estimator (230) to identify out-of-distribution (OOD) input data, i.e. data of type never before encountered by the disease prediction model in the CADx device and indicates to the user that an OOD input has been encountered and the score may be unreliable. Preferably, the input similarity estimator (230) contains of a distribution model for the training data and computes the similarity of the input data to the distribution function.

In a preferred embodiment of the invention the CADx device further comprises an output selector (235) to prevent a score (145) from being reported when an OOD input is encountered. Preferably, the CADx device provides a justification/explanation (135) for why an OOD occurred.

In an embodiment of the invention, the CADx device further comprises of an explanation generator (225) to indicates to the user the particular elements in the input data that have caused the input data to be an OOD input.

Figure 3:
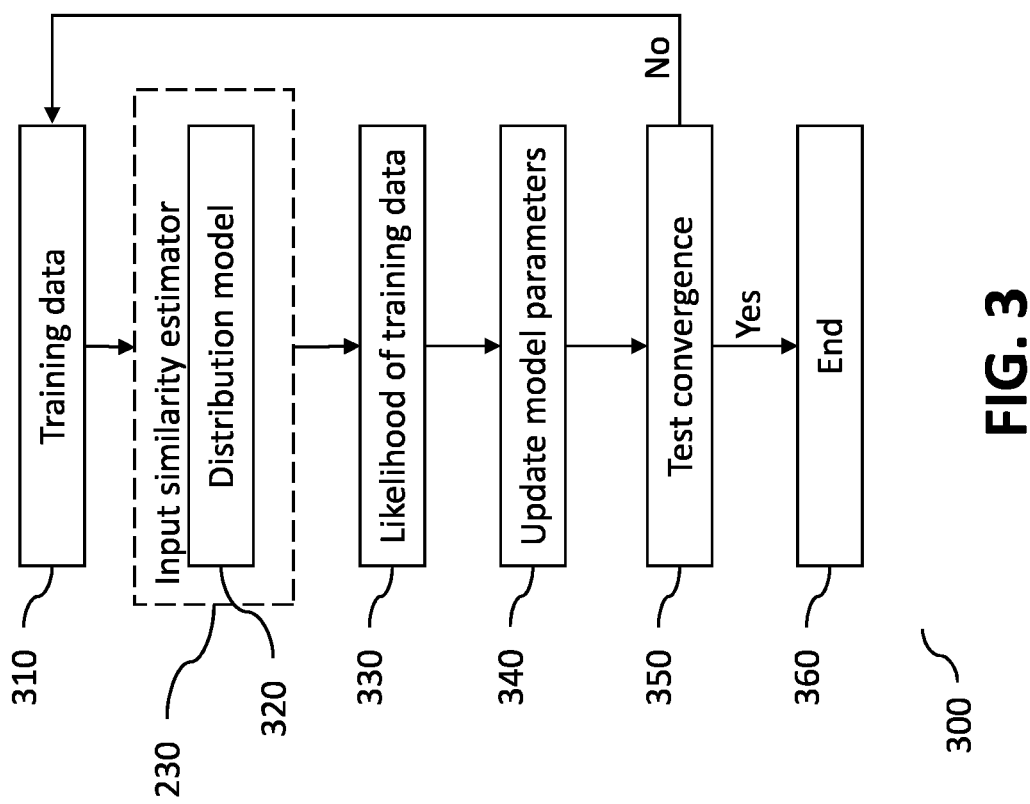
FIG. 3 shows an example of the fitting process of a distribution model for the training data.

In some examples of the invention, the distribution model $P_{train}$ of the training data is obtained by fitting a high-dimensional parametric distribution to the feature descriptors of the data units in the training data. An example diagram of the fitting process is shown in FIG. 3. The fitting process consists of finding a set of parameters in the input similarity estimator, $\theta$, of a distribution model (320) such that it models the distribution of the training data it is fitted to (310). At the $n^{th}$ iteration, this iterative fitting process proceeds by assessing the likelihood (330) of the training data (310) using the distribution model (320) with parameters $\theta_n$. Then, the model parameters are updated (340), $\theta \leftarrow \theta_{n+1}$, so as to increase the likelihood of the training data, $\Sigma_{\forall u \in U} P_{train}(F(x_u); \theta_n)$, where u is the index of one training datum and U is the set of indices of all training data. A convergence criterion is subsequently measured (350) to assess how much the likelihood improved in comparison with the previous iteration. For example, if the likelihood of the training data under the model from the $n^{th}$ iteration (i.e., with parameters $\theta_n$) improved by more than a small non-zero tolerance that is much smaller than one, the model has not converged, and the iterations continue. Otherwise, the fitting process ends (360). The final set of parameters $\theta$ are stored in the similarity estimator (230).

Examples of suitable distribution models (320) include the Gaussian Mixture Model (GMM), which can be fitted to the set of feature descriptors of the training data (310) using the expectation-maximization algorithm [Moon, T. K. (1996), *IEEE Signal processing magazine*, 13(6), pp. 47-60,] to update the model parameters (240), and the K-means models which can be fitted as described in [Pelleg, Dan; Moore, Andrew (1999). Proc. of $5^{th}$ ACM SIGKDD International Conference on Knowledge Discovery and Data Mining—KDD '99. San Diego, California, United States: ACM Press: 277-281].

In this example of the invention shown in FIG. 2, and where a GMM is used, the measure of input similarity for a unit of input data becomes $$\text{InputSimilarity}=P_{train}(v;\theta)=\Sigma_{i=1}^{k}\phi_i \mathcal{N}(v|\mu_i,\sigma_i) \quad (1.3).$$

Here, k is the number of Gaussian components of the GMM, and $\phi_i$, $\mu_i$ and $\sigma_i$ are respectively the weight, mean and covariance of the $i^{th}$ component, which make up the parameters $\theta$ of the GMM distribution.

The second computational element of the CADx device with gatekeeping is the rejection explanation generator (225). Its function is to compute an explanation for an input data unit being rejected by the
gatekeeper, which is communicated to the user in the event of an input data rejection. In some examples of the invention, the rejection explanation consists of an output-to-input attribution. In the context of data gatekeeping, the attribution-based explanation comprises of a set of scalars, each corresponding to one scalar in the input and proportional to the influence that the original value at that position had on the data rejection. For example, if the input data consists of an image I of dimensions N×M, where every position $I_{n,m}$ is an image intensity value, the attribution map A is also an N×M matrix where every position $A_{n,m}$ indicates the relative influence of $I_{n,m}$ on the rejection outcome. I is the raw input data. In the case of I being an image, "intensity" refers to the values of each voxel of the image. In addition to medical images, the input data may also include patient demographics and clinical history, as well as the outcome of related diagnostic tests such as blood biomarkers in the case of cancer diagnosis.

In some examples of the invention, where the input similarity is obtained through a GMM as given by (1.3), the output-to-input attribution map A is computed in the following way. A feature descriptor (215) $v_s$ is obtained by processing the unit of input data with the feature encoder (210). The distance between $v_s$ and the mean µ of every GMM component is computed to determine the component closest to $v_s$. Finally, A is the gradient with respect to the input image I of the distance $d_{v_s}$ between $v_s$ and its closest GMM component. That is:

$$A = \frac{\partial d_{v_s}}{\partial I}, \quad (1.4)$$

where, in some examples of the invention, $d_{v_s}$ is an L2-norm computed as $$d_{v_s} = \mathrm{argmin}_{i \in k}(\|v_s - \mu_i\|_2) \quad (1.5).$$

In an embodiment of the invention the rejection generator computes regions in the input data that make the input data OOD by computing the gradient with respect to the distribution function of the training data.

In some example implementations of the CADx device, where the machine learning model is a deep neural network, equation 1.4 can be computed using the back-propagation algorithm [Rumelhart, D. E., Hinton, G. E. and Williams, R. J. (1986) *Nature*, 323(6088), pp. 533-536]. Preferably, the neural network is a recursive neural network The final element of the gatekeeping in the example implementation is the output selector (235), whose function is to select, between the disease risk score and the rejection explanation, which signal is given to the output circuit (140) of the CADx device, and hence presented to the user. In some examples of the invention, the output selector takes as input the output of the score calculator (220), the rejection explanation generator (225) and the input similarity estimator (230), where the latter provides the signal on which the selection of the output is done. In some examples of the invention, the selection between the outputs is done based on a similarity threshold $TH_{sim}$, below which the input data is rejected and the rejection explanation is selected. That is, $$CADx \ \mathrm{Output} = \begin{cases} DiseaseRiskscore, & InputSimilarity \geq TH_{sim} \\ RejectionExplanation, & InputSimilarity < TH_{sim} \end{cases} \quad (1.6)$$

Generally, setting $TH_{sim}$ is a process of assessing the trade-offs between a high $TH_{sim}$, which may rejects input images too frequently and negatively affect the usability of the CADx device, and a low $TH_{sim}$, which accepts too many input images and thus may miss many OOD data sets and does not fulfil the gatekeeping purpose, of preventing input from images that are not suitable for analysis by the CADx system. Therefore, $TH_{sim}$ must be set through a careful process of risk assessment of the specific use case of the CADx device.

As examples of scenarios with different considerations for selecting $TH_{sim}$, we have the following: i) the CADx device is used as a second reader for a clinician, and ii) the CADx device is used to rank a large set of input images in order to establish the priorities with which the clinician should review them. In the first case, if the gatekeeper fails to identify an image as an OOD sample and the CADx device reports a score for an image that should have been rejected as not acceptable, the clinician's duty of care still requires them to inspect the scored nodule in the input image and they make the final decision on whether the patient should be followed up or discharged. In the second scenario, however, a CADx failure due to OOD data on an input image such as a cancer nodule being scored as a clear benign, would make the case a low priority for the clinician. As a result, there may be a delay before the patient is reviewed and the cancer diagnosed. Therefore, the gatekeeper of the second scenario needs to be more conservative, i.e. have higher $TH_{sim}$, for the input images to the CADx system, than that of the first scenario.

In a further example of the invention, the input similarity generator (230) contains two distributions, the first distribution describing the distribution of training data and the second distribution describing the distribution of other data that is known to be outside the IFU, for instance: data known to have artifacts arising from patient motion, data known to have extensive noise, data known to contain metal implants that cause ray artifacts, or data known known to have large spacing between its axial slices. Both distributions can be obtained by fitting a Gaussian Mixture Model using expectation maximization and an input similarity (1.3) is calculated for the training data distribution, $P_{train}$, and the outside-IFU distribution, $P_{ifu}'$, with the CADx output calculated as follows:

$$CADx \ \mathrm{Output} = \begin{cases} DiseaseRiskscore, & P_{train} > P_{ifu}' \\ RejectionExplanation, & \mathrm{otherwise} \end{cases} \quad (1.7)$$

The advantage of (1.7) is that it obviates the need to select $TH_{sim}$ but it requires outside-IFU data to be identified in order to fit the outside-IFU data distribution. The outside-IFU data may also comprise of data known to be rare in the training data or known to problematic to assess.

In a further example of the invention, the input similarity generator (230) contains multiple different distributions, the first describing the distribution of training data and at least one additional distribution for each particular type of outside-IFU data, for instance: data known to have artifacts arising from patient motion, data known to have extensive noise, data known to contain metal implants that cause ray artifacts, or data known to have large spacing between its axial slices. All the distributions can be obtained by fitting a Gaussian Mixture Model using expectation maximization and an input similarity (1.3) is calculated for the training data distribution, $P_{train}$, and the distributions for each type of outside-IFU data, $P_j$, where the index, $j \in J$, indicates the type of outside-IFU distribution and J is the set of all types of outside-IFU data. The CADx output is calculated as follows:

$$CADx \text{ Output} = \begin{cases} DiseaseRiskscore, & P_{train} > P_j \forall j \in J \\ \text{argmax}_{j \in J} P_j, & \text{otherwise} \end{cases} \quad (1.8)$$

That is, if the likelihood of the input data under the model $P_{train}$ of the training data is greater than the likelihood under any of the outside-IFU distributions, then the CADx device outputs the disease risk score. Otherwise, the input data will be rejected and the output of the CADx device will inform the user of which type of outside-IFU data was more likely to correspond to the input data. This is done by computing under which of the J outside-IFU distributions the input data had the maximum likelihood. For example, if the input data that is rejected is more likely under the model of 'data with extensive noise', then the output of the CADx will inform the user about the data rejection being potentially caused by image noise. The advantage of using the threshold defined in equation (1.8) is that it informs the user about the type of non-IFU data that was encountered by including j in the output (135), better enabling the user to decide how to remedy the cause of the OOD error.

In a further embodiment of the invention, the input similarity estimator further comprises of a second distribution for data outside the indications for use, known to be rare, or known to be problematic to score, and OOD is redefined according to equation (1.7) to indicate input data that is more similar to outside-IFU/rare/problematic than to the training data.

A further embodiment of the invention further comprising of separate distributions each for a different type of outside-IFU and where the score explanation generator identifies which outside-IFU distribution resembles equation (1.8) the input data the most when the input data is OOD and the outside-IFU type is provided to the user via the output (135).

When deploying a CADx device, it is critical to have mechanisms for detecting and preventing misuse of the device. One of such undesired scenarios is using the CADx device to assess data that it is ill-prepared to assess. The common practice is for the CADx device manufactures to issue indications for use which detail conditions that the input data must comply with for the CADx device to operate as claimed. However, there are scenarios such as subjective qualities of the input data or previously unknown features in the data, where the indications for use will be insufficient or impractical. To assure the safe use of the CADx device even in those unexpected scenarios, this invention builds an automatic gatekeeping system into a CADx device to further ensure that only applicable data is input to the CADx device. Moreover, in order to prevent the automatic rejection of input data from affecting the user experience and trust in the CADx device, this invention includes a mechanism that provides a level of explanation to the user as to why an input data was considered unapplicable and was rejected from evaluation.

This invention can be applied in any context where a CADx device, powered by a machine learning model, is used to assess the risk of disease from input medical data such as medical images.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A Computer Aided Diagnosis system for analysing medical images and determining if the images are acceptable for analysis, by determining if the images contain out-of-distribution input data, wherein out-of-distribution input data refers to data that is not well represented by the training data used to train the neural network that computes the disease risk score comprising:
   an input circuit for receiving at least one medical image, wherein the input circuit further comprises an input data encoder to transform the input data into a feature descriptor which comprises an intermediate numerical representation of the input data, wherein the feature descriptor is a vector containing scalar values that encode the input data according to the strength of the patterns of data within input data that a neural network has been trained to recognise as salient to computing a disease risk score;
   a gatekeeper circuit for determining if the at least one received medical image contains out-of-distribution input data and so does not meet the requirements of the Computer Aided Diagnosis, system for acceptable images,
   a rejection explanation generator to generate an output of why the received medical image is not suitable for analysis by the Computer Aided Diagnosis system, wherein the explanation is generated by at least one of:
   an output-to-input attribution based on a set of scalar values, each corresponding to each scalar that makes up the input medical image, and with a value proportional to the influence that the corresponding input scalar had on the rejection of the medical image;
   estimating the likelihood of the input medical image under a model fitted to the training data and data considered out-of-distribution, and determining under which of the out-of-distribution modes the input is most likely;
   and
   an output circuit to produce an output that is either a determination that the at least one received medical image contains out-of-distribution data and is not suitable for analysis by the Computer Aided Diagnosis, system, alongside the generated rejection explanation or a determination that the medical image is acceptable.

2. The Computer Aided Diagnosis system according to claim 1, wherein the output further comprises:
   a disease risk score that is output when the gatekeeper circuit determines that the at least one received medical image is acceptable for analysis by the Computer Aided Diagnosis system.

3. The Computer Aided Diagnosis-system according to claim 1, wherein the input image is one of: a Computed Tomography image, an Magnetic Resonance Imaging image, a Positron Emission Tomography image, an X-ray image, an ultrasound image or a Single Photon Emission Tomography image.

4. The Computer Aided Diagnosis system according to claim 1, wherein the input further comprises one or more of: biomarkers for the patient or clinical parameters for the patient.

5. The Computer Aided Diagnosis system according to claim 4, wherein the biomarkers and clinical parameters comprise at least one of: patient age, patient sex, results of blood tests, results of lung function tests.

6. The Computer Aided Diagnosis system according to claim 1, wherein the gatekeeper circuit further comprises an input similarity estimator that can compare the received input image to a distribution model derived from training data to determine if the input image contains out-of-distribution input data.

7. The Computer Aided Diagnosis system according to claim 6, wherein the distribution model is a model of the probability distribution of the training data.

8. The Computer Aided Diagnosis system according to claim 7, wherein the input similarity estimator further comprises a second distribution model for specific out-of-distribution data, and the input similarity estimator indicates input data that is closer to the second distribution model rather than the training data.

9. The Computer Aided Diagnosis system according to claim 7, wherein the input similarity estimator comprises a plurality of different distribution models, and wherein the output circuit can provide an output that the image is out-of-distribution data and also indicate which distribution model most resembles the input image with out-of-distribution data.

10. The Computer Aided Diagnosis system according to claim 1, wherein the feature descriptor provides an input to a score calculator for determining a disease risk score for the input medical image.

11. The Computer Aided Diagnosis system according to claim 10, wherein the feature descriptor is input to at least one of a rejection explanation generator and an input similarity estimator of the gatekeeper circuit.

12. The Computer Aided Diagnosis system according to claim 11, wherein at least one of the rejection explanation generator and a score calculator provide an output to an output selector.

13. The Computer Aided Diagnosis system according to claim 12, wherein the rejection explanation generator determines an attribution map A for the input medical image for each pixel of the image to generate the output that the image is not suitable for analysis.

14. The Computer Aided Diagnosis, system according to claim 13, wherein the rejection explanation generator determines the attribution map A by calculating the distance between the input data and distribution model and further calculating the derivative of the distance with respect to the input image.

15. The Computer Aided Diagnosis system according to claim 14, wherein the output selector will select either a disease risk score if the medical image is acceptable, or an explanation of the reason that the image is not suitable for analysis as the output from the CADx system.

16. The Computer Aided Diagnosis system according to claim 15, wherein the output selector compares the output of the input similarity estimator to a threshold to determine if the input data should be rejected as containing out-of-distribution data.

17. The Computer Aided Diagnosis system according to claim 16, wherein the threshold is used to determine the Computer Aided Diagnosis, output such that:

$CADx$ Output =
$$\begin{cases} DiseaseRiskscore, & InputSimilarity \geq \text{Similarity Threshold} \\ RejectionExplanation, & InputSimilarity < \text{Similarity Threshold} \end{cases}$$

where Similarity Threshold is a process of assessing the trade-offs between a high Similarity Threshold, and a low Similarity Threshold.

* * * * *